United States Patent
Kwun et al.

(10) Patent No.: US 6,295,677 B1
(45) Date of Patent: Oct. 2, 2001

(54) METHOD FOR INSPECTING LIQUID FILLED PIPES USING MAGNETOSTRICTIVE SENSORS

(75) Inventors: Hegeon Kwun; Keith A. Bartels, both of San Antonio, TX (US)

(73) Assignee: Southwest Research Institute, San Antonio, TX (US)

( * ) Notice: Subject to any disclaimer, the term of this patent is extended or adjusted under 35 U.S.C. 154(b) by 0 days.

(21) Appl. No.: 09/469,423

(22) Filed: Dec. 23, 1999

(51) Int. Cl.$^7$ .......................... G01N 29/08; G01N 29/14
(52) U.S. Cl. .................................. 7/602; 73/622
(58) Field of Search .......................... 73/622, 623, 587, 73/602, 592, 594, 597, 598, 599, 600

(56) References Cited

U.S. PATENT DOCUMENTS

| | | | |
|---|---|---|---|
| 4,428,235 | * 1/1984 | Sugiyama | 73/579 |
| 4,577,503 | 3/1986 | Imaino et al. | 73/602 |
| 4,937,767 | 6/1990 | Reuschel et al. | 364/570 |
| 5,144,389 | 9/1992 | Lochner | 73/609 |
| 5,404,754 | 4/1995 | Wang | 73/602 |
| 5,425,272 | 6/1995 | Rhodes et al. | 73/579 |
| 5,458,120 | 10/1995 | Lorraine | 128/63.01 |
| 5,537,876 | 7/1996 | Davidson et al. | 73/624 |
| 5,549,111 | 8/1996 | Wright et al. | 128/742 |
| 5,581,037 | * 12/1996 | Kwun et al. | 73/623 |
| 5,734,588 | * 3/1998 | Rose et al. | 364/507 |
| 5,970,434 | * 10/1999 | Brophy et al. | 702/170 |
| 6,000,288 | * 12/1999 | Kwun et al. | 73/597 |

* cited by examiner

Primary Examiner—Hezron Williams
Assistant Examiner—Rose M. Miller
(74) Attorney, Agent, or Firm—Cox & Smith Incorporated

(57) ABSTRACT

An improved method for defect detectability for the inspection of liquid filled pipes using magnetostrictive sensors. The improved method comprises first recognizing the liquid-induced changes in the dispersion properties of the second longitudinal wave mode, $L(0,2)$. These liquid-induced changes include a severe dispersion at periodic branching frequencies that result in a pulse-like characteristic in the extended received signal. A trailing portion of a received signal component associated with a geometric irregularity, is shown to comprise the branching frequency components. The trailing portion of the extended signal may therefore be removed in order to improve defect detection. The removal process comprises one of three alternative methods. A first method includes creating a short duration pulse free of the frequency components that comprise the trailing signals, and applying the pulse to a magnetostrictive transmitter, thereby generating a longitudinal wave signal in the pipe wall free of the trailing signal frequency components. A second method comprises transmitting a broadband signal and processing the detected signal through a digital filter that eliminates those frequency components known to comprise the trailing signals. A third method involves using a signal whose bandwidth lies in the region between two adjacent branching frequencies in the dispersion curve. The result is a detected signal within which components representative of irregularities are less extended and therefore less likely to override subsequent defect components in the detected signal.

12 Claims, 5 Drawing Sheets

METHOD FOR INSPECTING LIQUID FILLED PIPES USING MAGNETOSTRICTIVE SENSORS

BACKGROUND OF THE INVENTION

1. Field of the Invention

The present invention relates generally to methods for the Non-Destructive Evaluation (NDE) of pipes and tubes using magnetostrictive sensor technologies. The present invention relates more specifically to an improved method for detecting defects by manipulating the frequency characteristics of the transmitted and/or received signals associated with the use of magnetostrictive sensor technologies for the inspection of pipes and tubes.

2. Description of the Related Art

Magnetostrictive sensor technologies have been used successfully for a period of time with the inspection of pipes and tubes in processing plants such as refineries, chemical plants, steam process plants and the like. Examples of the use of magnetostrictive sensors, and the various analytical techniques associated therewith, are disclosed in U.S. Pat. Nos. 5,456,113 and 5,457,994, each entitled Non-Destructive Evaluation of Steel Cables and Ropes Using Magnetostrictively Induced Ultrasonic Waves and Magnetostrictively Detected Acoustic Emissions, as well as U.S. Pat. No. 5,581,037 entitled Non-Destructive Evaluation of Pipes and Tubes Using Magnetostrictive Sensors, all of which are commonly owned by the assignee of the present invention, Southwest Research Institute.

The techniques associated with such NDE inspections of pipes, tubes, cables and the like typically involve generating longitudinal waves along the length of the pipe or tube and analyzing signals that are reflected from defects and anomalies within the pipe or tube. One of the many advantages of this technique is the ability to detect defects by sensing the reflected signal at the same physical location at which the interrogating signal waves are generated.

Because mechanical waves generated by magnetostrictive sensors can propagate a long distance through a structure under inspection the techniques are capable of inspecting very long or large segments, typically more than a hundred feet under favorable conditions, of pipe very rapidly. These techniques also provide a complete volumetric inspection of a long section of pipe with minimum ancillary activity such as surface preparation, scaffolding, or insulation removal. These magnetostrictive sensor methods therefore offer a very efficient and comprehensive mechanism for pipe and tube inspection.

In general, the longitudinal wave modes utilized in the above referenced techniques for inspection are dispersive in nature. This means that the velocity of the mechanical wave propagation varies with the wave frequency. Various factors affect the dispersion characteristics of a transmitted signal containing broad frequency components. Primary among these factors are pipe geometry (diameter and wall thickness) and the presence or absence of a fluid within the pipe. Properly understood, the dispersive nature of the wave modes utilized in pipe inspection can assist in the identification of relevant anomalies and geometric irregularities in the pipe.

Examples of previous attempts in the prior art to improve the defect detectability of NDE sensors include the following patents:

U.S. Pat. No. 5,612,495 issued to Shimada et al. on Mar. 18, 1997, entitled Non-Destructive Examination Device, describes a system that uses magnetostrictive transmitters and response sensors to carry out the non-destructive evaluation of a material. The system anticipates the use of a resonant frequency for the interrogating signal.

U.S. Pat. No. 5,526,689 issued to Coulter et al. on Jun. 18, 1996, entitled Acoustic Emission for Detection of Corrosion Under Insulation, describes a method and apparatus for detecting the presence of surface corrosion under insulation on a pipe structure. This patent anticipates the use of a broadband of acoustic waves to interrogate the structure. The signal analysis method in Coulter et al. involves producing RMS voltage signals indicative of the detected sound waves and comparing the RMS voltage signals to standard signals obtained from uncorroded piping. The analysis involves a strict amplitude comparison to distinguish the signal component from the defect.

U.S. Pat. No. 5,195,046 issued to Gerardi et al. on Mar. 16, 1993, entitled Method and Apparatus for Structural Integrity Monitoring, describes a piezoelectric transducer based system designed for the detection, monitoring, and analysis of such materials as aircraft structures. Various pattern recognition techniques are utilized. The patent lists 25 illustrative features (column 11) that include both time and frequency domain parameters as providing the basis for pattern recognition.

U.S. Pat. No. 5,665,913 issued to Chung on Sep. 9, 1997, entitled Method and Apparatus for Evaluation and Inspection of Composite-Repaired Structures, describes a system and method for NDE of composite-repaired structures wherein the signal transmitters and sensors are piezoelectric based devices. The system anticipates the use of either a single frequency for interrogating the material or a range of frequencies.

U.S. Pat. No. 5,469,060 issued to Meyerand on Nov. 21, 1995 entitled Time Encoded Magnetic Resonance Imaging, describes a system that utilizes a separate set of signal transducers and applies a resonant frequency pulse to the material under investigation. The RF signals received as a function of time are converted to a set of frequency domain functions at specific times relating to specific strips in the image being generated.

U.S. Pat. No. 5,574,639 issued to Qian et al. on Nov. 12, 1996, entitled System and Method for Constructing Filters for Detecting Signals Whose Frequency Content Varies With Time, is generally directed to a signal analysis method intended to reliably detect the presence of signals of interest, especially those whose frequency content varies with time. The Qian et al. invention is directed to the development and use of time templates designed to match the received signal of interest. The patent applies the Gabor Spectrogram to a computer representation of the signals in the joint time-frequency domain for the purpose for instantaneous frequency estimation.

U.S. Pat. No. 5,144,839 issued to Lochner on Sep. 8, 1992 entitled Method of Checking the Presence of a Pipeline Connection Between Two End Points, describes a method for detecting pipe junctures with an acoustic signal whose frequency has been selected to be above the frequency of ambient noises and below an upper limit related to the geometry of the pipe and the acoustic velocity of the material in the pipe.

U.S. Pat. No. 4,937,767 issued to Reuschel et al. on Jun. 26, 1990 entitled Method and Apparatus for Adjusting the Intensity Profile of an Ultrasound Beam, describes an ultrasonic imaging system having adjustable signal sources such that the duration of the drive pulse can be varied. In the case of ultrasonic signal generators (piezoelectric crystals), signal amplitude may be varied by changing the drive frequency around the crystal's resonant frequency.

U.S. Pat. No. 5,425,272 issued to Rhodes et al. on Jun. 20, 1995 entitled Relative Resonant Frequency Shifts to Detects Cracks, describes yet another ultrasonic measurement method that utilizes the ratio of two prominent resonant response frequencies to characterize the physical characteristics of a part.

U.S. Pat. No. 5,549,111 issued to Wight et al. on Aug. 27, 1996 entitled Method and Apparatus for Adjustable Frequency Scanning in Ultrasound Imaging, describes an ultrasonic system that utilizes an energy pulse having a carrier frequency higher in the center of the field of view than at the edges. A corresponding method for demodulation of the received signal is also described. In each case, it is a directional variable that is modified by means of the frequency variations.

U.S. Pat. No. 5,537,876 issued to Davidson et al. on Jul. 23, 1996 entitled Apparatus and Method for Non-Destructive Evaluation of Butt Welds, describes a system for interrogating welds in sheet material using horizontal shear ultrasonic waves generated on the surface. The apparatus described detects only reflected horizontal shear waves by electronically filtering out other modes that occur at different frequencies. The system utilizes electromagnetic acoustical transducers (EMAT) as both transmitters and receivers for the ultrasonic waves.

While utilizing a broadband interrogating signal with magnetostrictive sensor techniques generally facilitates the acquisition of a large quantity information by broadly "illuminating" the geometric and material features of the pipe or tube under investigation, this same quantity of information carried in the detected signal often becomes too complex to adequately analyze. It would be desirable, therefore, to gain the benefits of a broadband interrogating signal while still reducing the detected signal to an interpretable complexity. The present invention addresses one such signal complexity that can be appropriately eliminated or reduced to the point where otherwise obscured signal characteristics can be identified.

SUMMARY OF THE INVENTION

It is therefore an object of the present invention to provide a method for improved defect detectability utilizing magnetostrictive sensor technologies for pipe and tube inspection.

It is further object of the present invention to provide a method for improved defect detectability using magnetostrictive sensor technologies for pipe and/or tube inspection that permits the discrimination of signal components indicative of defects and anomalies of interest that would otherwise be obscured by signal components related to the presence of a liquid within the pipe or tube.

It is a further object of the present invention to provide an improved method for defect detectability using magnetostrictive sensor technologies for pipe and/or tube inspection that eliminates or reduces obscuring signal components related to the presence of a liquid within the pipe or tube, by manipulating the frequency characteristics of the transmitted and/or the detected signals.

It is yet another object of the present invention to provide a method for improved defect detectability using magnetostrictive sensor technologies for piping inspection that provides analysis techniques capable of identifying the dispersive characteristics of a liquid filled pipe and utilizing such information to partially nullify non-relevant detected signal components in order to discriminate otherwise obscured signal components associated with defects and anomalies of interest.

In fulfillment of these and other objectives, the present invention provides an improved method for defect detectability for the inspection of liquid filled pipes using magnetostrictive sensors. The improved method comprises first recognizing the liquid-induced changes in the dispersion properties of the second longitudinal wave mode, L(0,2). These liquid-induced changes include a severe dispersion at periodic branching frequencies that result in a pulse-like characteristic in the extended received signal. A trailing portion of a received signal component associated with a geometric irregularity, is shown to comprise the branching frequency components. The trailing portion of the extended signal may therefore be removed in order to improve defect detection. The removal process comprises one of three alternative methods. A first method includes creating a short duration pulse free of the frequency components that comprise the trailing signals, and applying the pulse to a magnetostrictive transmitter, thereby generating a longitudinal wave signal in the pipe wall free of the trailing signal frequency components. A second method comprises transmitting a broadband signal and processing the detected signal through a digital or analog filter that eliminates those frequency components known to comprise the trailing signals. A third method involves using a signal whose bandwidth lies in the region between two adjacent branching frequencies in the dispersion curve. The result is a detected signal within which components representative of irregularities are less extended and therefore less likely to override subsequent defect components in the detected signal.

BRIEF DESCRIPTION OF THE DRAWINGS

FIG. 3b is a graphical representation of the frequency spectrum of the leading portion of the signal shown in FIG. 3a.

FIG. 3c is a graphical representation of the frequency spectrum of the trailing portion of the signal shown in FIG. 3a.

DETAILED DESCRIPTION OF THE PREFERRED EMBODIMENTS

In general, the present invention describes methods for reducing the time-extent of reflected signals received during the inspection of liquid filled pipes utilizing magnetostrictive sensors. By reducing the time-extent of the reflected signals, defect detection capabilities are improved.

It has often been observed that the signals reflected from geometric irregularities such as girth welds and defects in pipes, tubes, and the like, have a long duration and consist of a series of shorter duration signals. This can readily be seen in the detected signal (10) represented in FIG. 1. These long duration signals consisting of small pulses can mask signals reflected from defects and therefore complicate defect detection.

Figure 1:
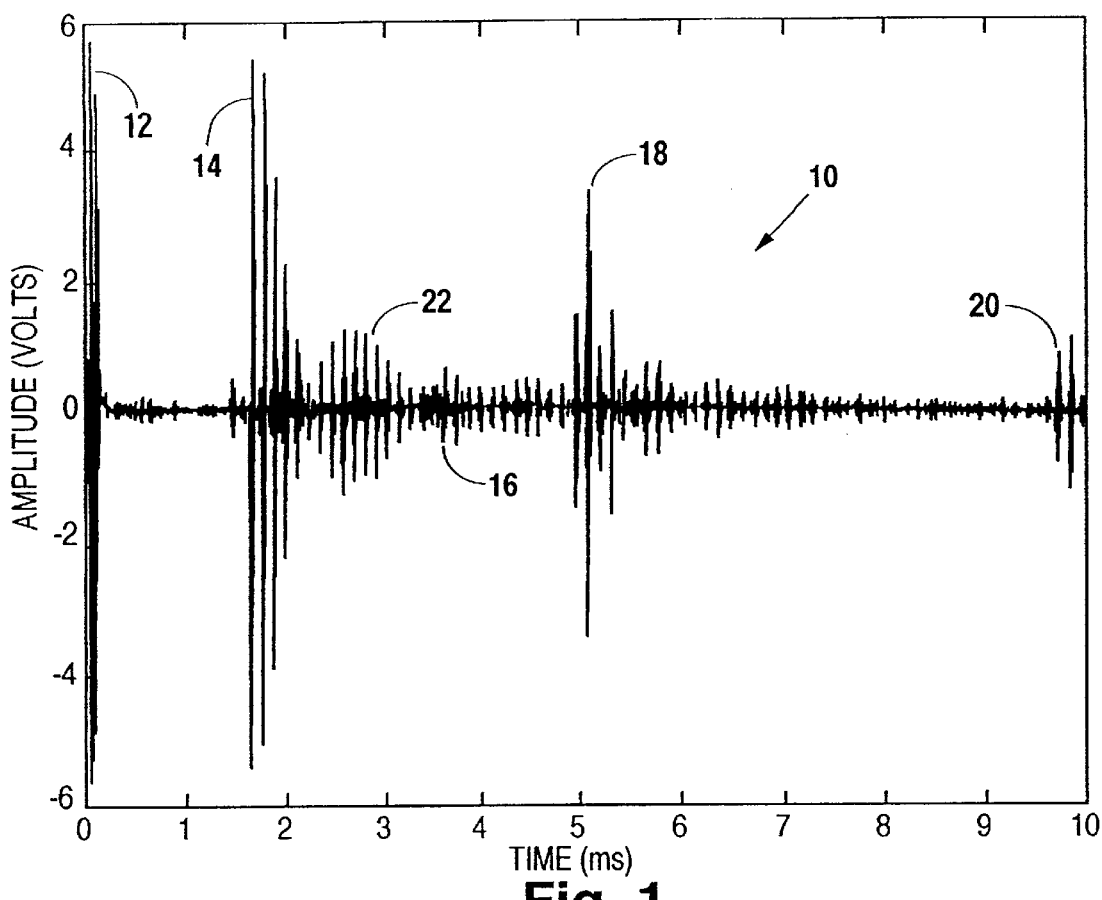
FIG. 1 is a graphical representation of a prior art detected signal from a liquid filled line in a refinery.

The detected signal (10) shown in FIG. 1 comprises a number of relevant signal components, many of which exhibit this pulsed characteristic. These signal components include the initial pulse (12), weld reflection pulse (14), defect reflection pulse (16) weld reflection pulse (18), and weld reflection pulse (20). Little more is discernable in the complex "pulsed structure" of the detected signal shown in FIG. 1. Signal component (22), for example, is in fact the trailing portion of the reflected weld component (14). If any further defects existed between weld (14) and defect (16), they would be difficult to discern beneath the trailing wave components (22) of weld signal component (14).

Figure 2:
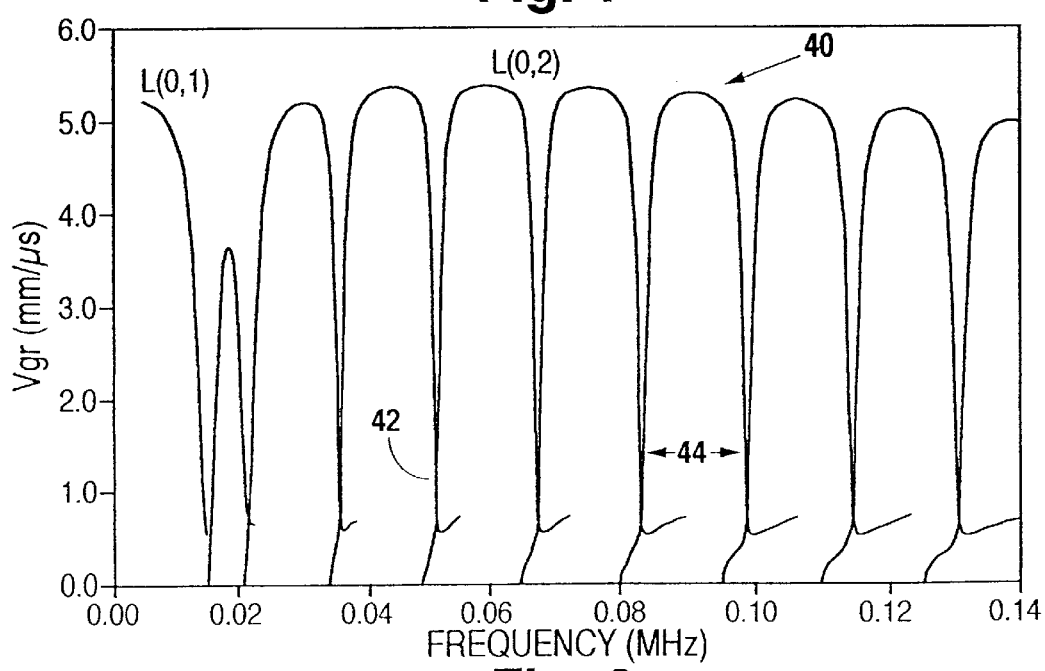
FIG. 2 is a graphical representation of the calculated dispersion curves for the L(0,1) and L(0,2) modes showing group velocity versus frequency for a first example of a liquid filled pipe.

The pulse-like nature of the signals is caused by the liquid-induced changes in the dispersion properties of the second longitudinal wave mode, L(0,2), typically used for piping inspection. Reference is made to FIG. 2 for an illustration of the changes in the dispersion curves for the L(0,2) mode when a pipe is filled with water. As can be seen in this example, the liquid in the pipe causes the dispersion curve (40) to be branched into regions separated by approximately the same frequency interval (44). The severe dispersion (42) at the branching frequencies indicates a large reduction in group velocity. The periodic occurrence of the branching frequencies causes the observed pulse-like behavior in the detected signal when the received signal results from a transmitted signal deriving from a short duration pulse. As indicated above, the dispersion characteristics are influenced by the pipe geometry and the presence of a liquid within the pipe. The dispersion curves shown in FIG. 2 are calculated for the L(0,1) and L(0,2) modes in a 4.5 inch (114.3 mm) outside diameter, schedule 80 pipe filled with water. Any given liquid filled pipe or tube may have a corresponding dispersion curve calculated with the resultant branching frequencies determined.

Figure 3A:
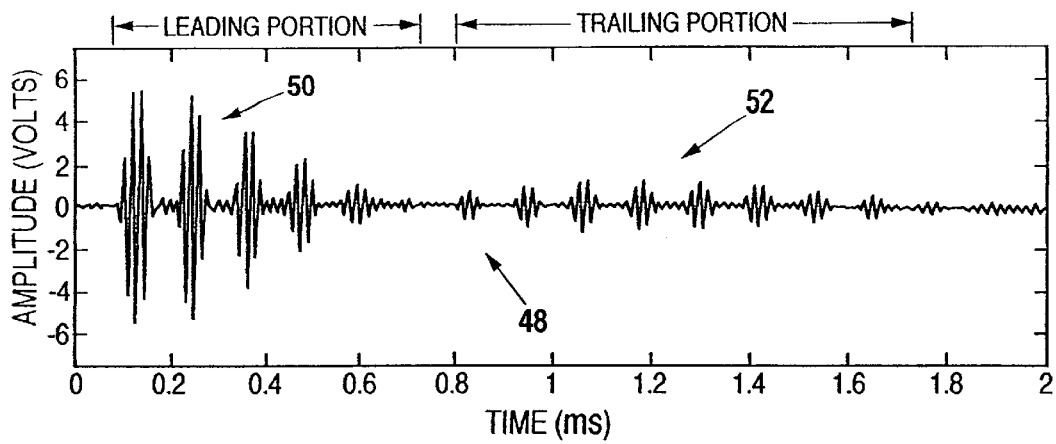
FIG. 3a is a graphical representation of an expanded view of a long duration signal from a first weld signal component such as those shown in FIG. 1.
Figure 3B:
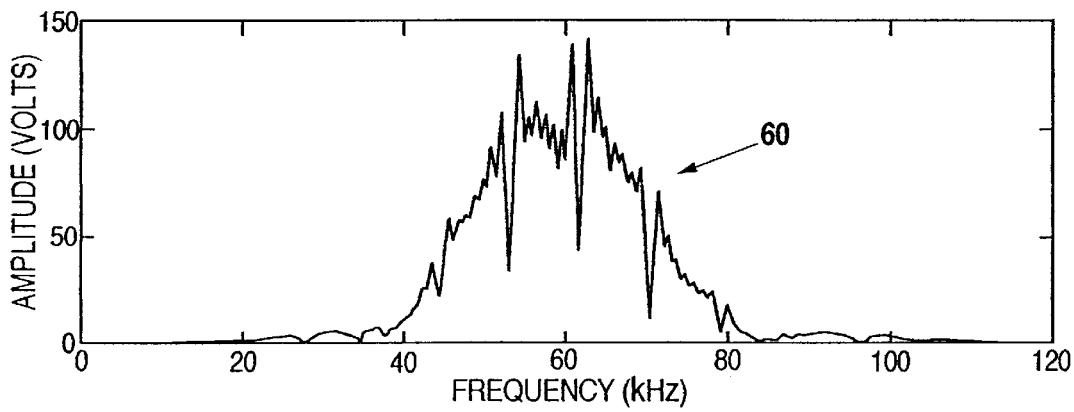
Figure 3C:
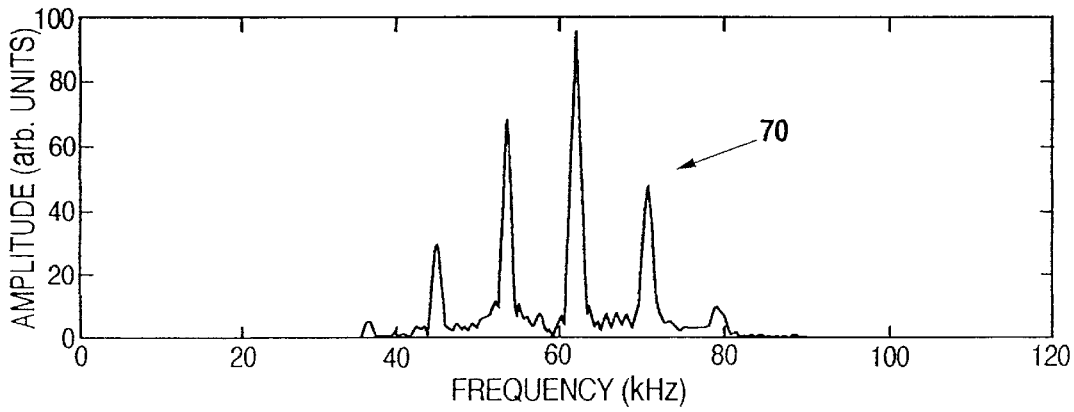

Reference is now made to FIGS. 3a–3c for a description of the analysis of the signal components in question. FIG. 3a represents an expanded view of the long duration signal (48) from a first weld such as is shown in the detected signal represented in FIG. 1. In this view (FIG. 3a) it can be seen that the signal (48) comprises a leading portion (50) and a trailing portion (52).

The same pulsed spacing can be seen within both the leading portion (50) of the signal (48) and the trailing portion (52). This reflects the large reduction in group velocity for periodic frequencies (the branching frequencies).

Analysis of each portion of the expanded long duration signal (48) reveals that the leading portion (50) of the extended received signal (48) is devoid of those frequency components around the branching frequencies identified in FIG. 2. The frequency content (60) of the leading portion (52) is seen in FIG. 3b to exhibit gaps at and around the branching frequencies. The frequency content (70) of the trailing portion (52), on the other hand (shown in FIG. 3c), is found to be comprised primarily of frequency components around the branching frequencies.

If the frequency components comprising the trailing portion (52) of the signal are removed, the overall time extent of the signal component (48) will correspondingly be reduced. This will improve the defect detection capability of the magnetostrictive technique by "uncovering" additional signal components potentially representative of further defects that were previously missed.

Since the physical laws governing mode dispersion cannot be altered, the method of the present invention achieves this same effect by removing the frequency components that bring about the trailing portion of the signal, from either the transmitted wave signal or from the received wave signal.

FIRST PREFERRED METHOD OF THE INVENTION

Removing the frequency components comprising the trailing portion of the signal can be accomplished in a number of ways. A first preferred method comprises creating a short duration pulse that does not have the frequency components that comprise the trailing signals. As indicated above, the branching frequencies can, for any specific liquid filled pipe, be determined and used to manipulate the interrogating signal pulse. This can be accomplished by using an arbitrary wave form generator or a digital to analog converter. This is distinguished from prior art magnetostrictive sensor systems that typically use a short duration sinusoidal pulse that contains broad frequency components typically including those that comprise the trailing signals.

The first preferred method of the present invention then applies the above mentioned pulse to the magnetostrictive sensor transmitter which thereby generates a longitudinal wave signal in the pipe wall that is free of the frequency components comprising the trailing signal. In this manner the detected signal such as that shown in FIG. 4, will likewise be free from the sequence of trailing signal components that might otherwise obscure subsequent defects or other geometric irregularities in the pipe. The signal components shown in FIG. 4 are described in more detail below.

SECOND PREFERRED METHOD OF THE INVENTION

A corollary method to the above described first preferred method involves modification of the detected signal rather than the transmitted signal. A first step of this corollary method comprises transmitting a broadband signal as is the typical practice in current magnetostrictive sensor systems. The second step of the method involves processing the detected signal through a digital or analog filter that nullifies those frequency components comprising the trailing signals in order to reduce the trailing signal amplitude. With this second method, the transmitting magnetostrictive sensor generates both wanted and unwanted frequency components. The efficiency of this second method is somewhat less than that of the first preferred method described above because the signal is cleared of unwanted frequency components only after its interrogating pass through the pipe.

Figure 4:
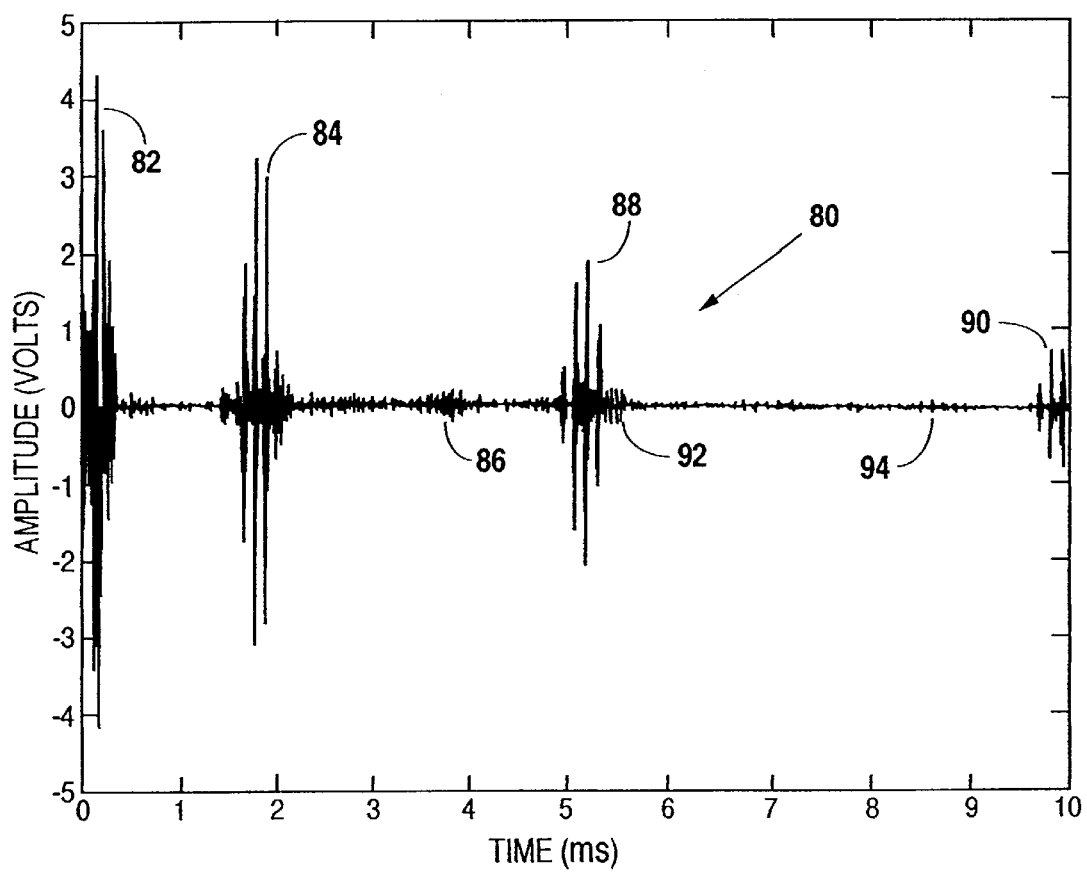
FIG. 4 is a graphical representation of a detected signal after processing using the second preferred method of the present invention.
Figure 5:
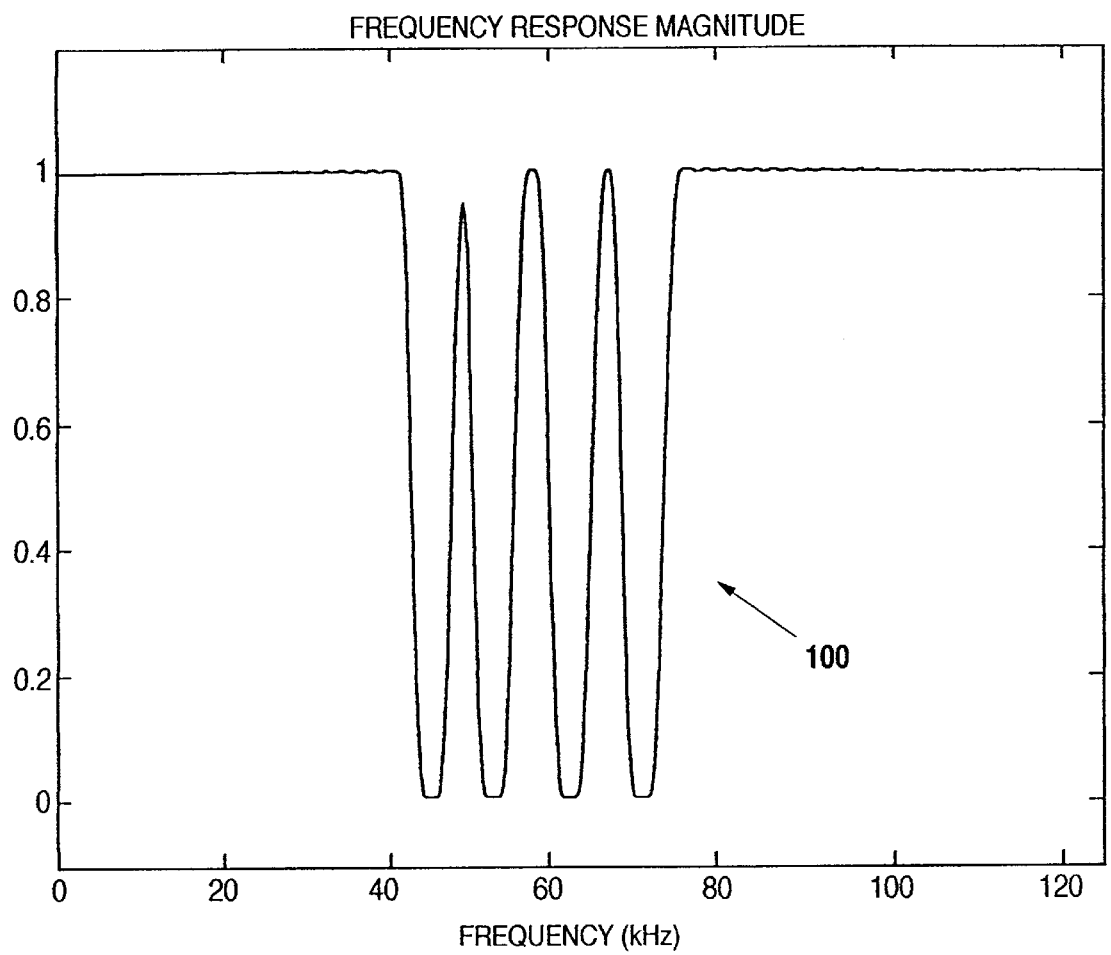
FIG. 5 is a graphical representation of the magnitude of the frequency response of a digital filter utilized to obtain the detected signal data shown in FIG. 4.

FIG. 4 also provides an example of the level of improvement gained by implementing the second method of the present invention on the data shown in FIG. 1. The magnitude of the frequency response of the digital or analog filter (100) utilized in this example is shown in FIG. 5.

As can be seen in FIG. 4, the received signal (80) comprises signal components that are significantly shorter in duration after processing, thus permitting defect indications to appear that were not otherwise recognizable before the processing. Equivalently, the data shown in FIG. 4 could be obtained by the first method of the present invention by way of applying the signal (110) shown in FIG. 6 to the magnetostrictive sensor transmitter. The frequency content of the signal (110) in FIG. 6 is the same as the spectrum of the filter (100) shown in FIG. 5.

Figure 6:
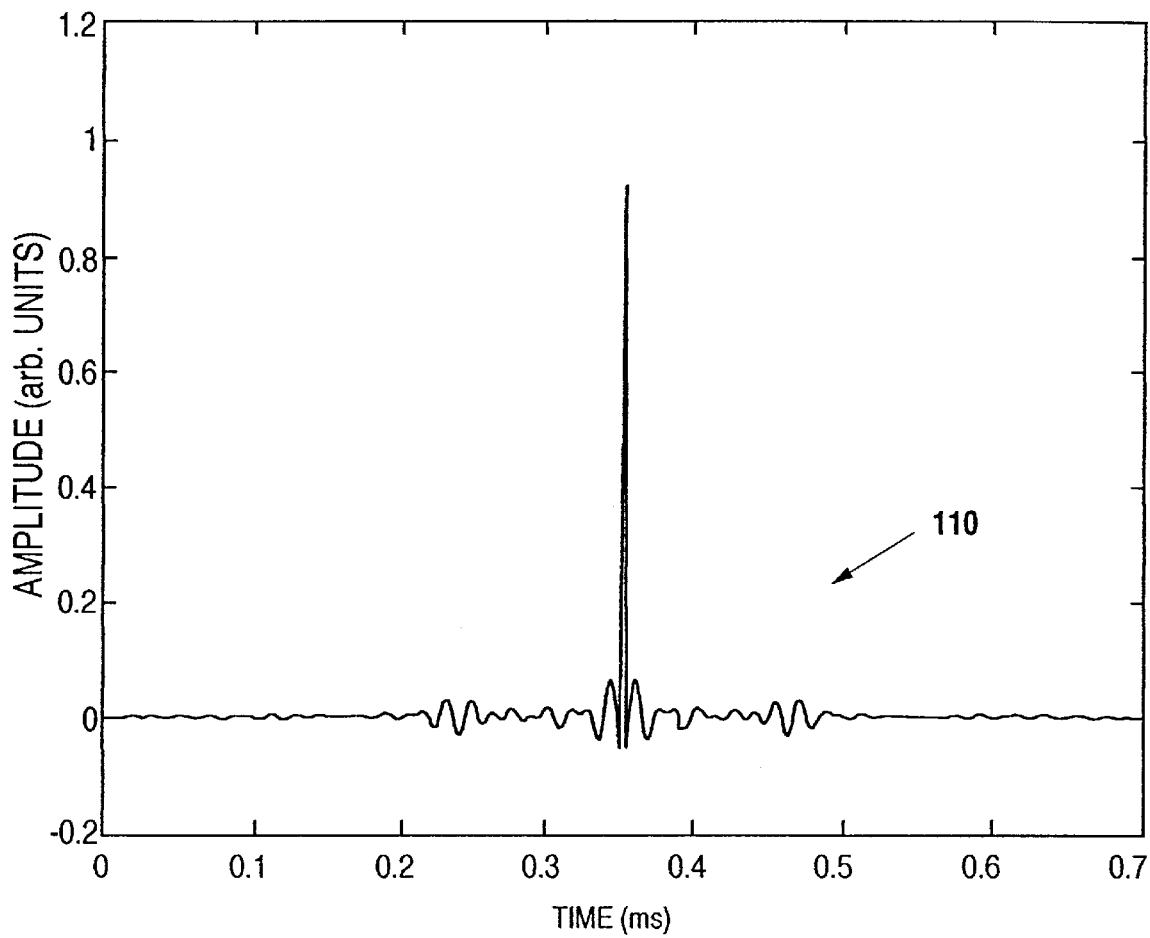
FIG. 6 is a graphical representation of a pulse-transmitted signal utilized to obtain the detected signal data shown in FIG. 4 according to the first preferred method of the present invention.

FIG. 6 therefore represents an appropriate short duration pulse to be applied to a magnetostrictive sensor, that differs from the prior art broadband sinusoidal pulse, in that the branching frequencies previously identified (calculated) according to the dispersion curves shown in FIG. 2, are absent from the frequency spectrum of the signal. A detected signal (80) such as shown in FIG. 4 is the expected result of the implementation of the first preferred method of the present invention.

The received signal (80) in FIG. 4 retains the primary signal components that were present in the unprocessed signal (10) shown in FIG. 1. Initial component (82) is followed by weld signal component (84), defect signal component (86), weld signal component (88) and weld signal component (90). Additionally discernable in the received signal (80), however, are defect signal component (92), which follows immediately after weld signal component (88) and was previously obscured by the trailing component of weld signal (88), and defect signal component (94), which was previously indistinguishable from the "background" pulses in the signal.

FIG. 5 represents the magnitude of the frequency response of an appropriate digital filter (100) to be applied to the output of a magnetostrictive sensor used to receive the reflected signal from the liquid filled pipe. As can be seen from the frequency profile in FIG. 5, this has the effect of nulling those trailing components associated with the branching frequencies identified for the liquid filled pipe under inspection (see FIG. 2). This effect is seen in conjunction with each signal component associated with a geometric irregularity in the overall signal (80) detected. That is, trailing signal components for each weld signal component and each defect signal component are reduced to an extent that the discrete effect that an irregularity has on the overall received signal is narrowed.

THIRD PREFERRED METHOD OF THE INVENTION

Yet another method for implementing the basic concepts of the present invention comprises utilizing an initial signal having a band width that lies within the region between two adjacent branching frequencies in the dispersion curve (FIG. 2). This is a departure from the first method described above which, although it removes the branching frequencies from the initial signal, still retains a relatively broadband profile. In the third method, the detected signal is processed through a narrow bandpass filter centered around the frequency chosen for wave transmission. As an expected result of this reduction in bandwidth, the third method will degrade the spatial resolution of the interrogating signal and is therefore less attractive than the two previous methods described above.

Although the present invention has been described with reference to specific embodiments, this description is not meant to be construed in a limited sense. Various modifications of the disclosed preferred methods, as well as alternative methods, will become apparent to those persons skilled in the art upon reference to the description of the invention, the drawings, and the following claims.

We claim:

1. A method for improved defect detectability in the inspection of liquid filled pipes using magnetostrictive sensors, the method comprising the steps of:

calculating dispersion curves for the second longitudinal wave mode for said liquid filled pipe under inspection;

identifying a plurality of branching frequencies in said dispersion curves, said branching frequencies representing periodic reductions in wave group velocities caused by said liquid in said pipe;

generating a short duration pulse having frequencies exclusive of said branching frequencies;

applying said short duration pulse to a magnetostrictive sensor transmitter, thereby generating a longitudinal wave signal in said liquid filled pipe free of said branching frequency components; and receiving a detected signal with a magnetostrictive sensor receiver, said detected signal having discernable signal components indicative of geometric irregularities in said liquid filled pipe.

2. The method of claim 1 wherein said step of calculating dispersion curves comprises identifying a pipe geometry factor and a liquid factor, and utilizing said factors to establish dispersion characteristics for a nominal broadband signal within said liquid filled pipe.

3. The method of claim 1 wherein said step of calculating dispersion curves comprises interrogating said liquid filled pipe with a nominal broadband signal and analyzing a received signal to establish dispersion characteristics.

4. The method of claim 1 wherein said step of generating a short duration pulse comprises utilizing an arbitrary waveform generator set to exclude said branching frequencies.

5. The method of claim 1 wherein said step of generating a short duration pulse comprises utilizing a digital to analog convertor programmed to exclude said branching frequencies.

6. A method for improved defect detectability in the inspection of liquid filled pipes using magnetostrictive sensors, the method comprising the steps of:

calculating dispersion curves for the second longitudinal wave mode for said liquid filled pipe under inspection;

identifying a plurality of branching frequencies in said dispersion curves, said branching frequencies representing periodic reductions in wave group velocities caused by said liquid in said pipe;

generating a short duration sinusoidal pulse having broad frequency components;

applying said short duration sinusoidal pulse to a magnetostrictive sensor transmitter, thereby generating a longitudinal wave signal in said liquid filled pipe;

receiving a detected signal with a magnetostrictive sensor receiver, from said liquid filled pipe; and filtering said detected signal through a signal filter, said signal filter removing those frequency components comprising said branching frequencies.

7. The method of claim 6 wherein said step of calculating dispersion curves comprises identifying a pipe geometry factor and a liquid factor, and utilizing said factors to establish dispersion characteristics for a nominal broadband signal within said liquid filled pipe.

8. The method of claim 6 wherein said step of calculating dispersion curves comprises interrogating said liquid filled pipe with a nominal broadband signal and analyzing a received signal to establish dispersion characteristics.

9. The method of claim 6 wherein said step of filtering said detected signal through a signal filter comprises adding said signal to a nullifying signal zeroed at a plurality of said branching frequencies.

10. A method for improved defect detectability in the inspection of liquid filled pipes using magnetostrictive sensors, the method comprising the steps of:

calculating dispersion curves for the second longitudinal wave mode for said liquid filled pipe under inspection;

identifying a plurality of branching frequencies in said dispersion curves, said branching frequencies representing periodic reductions in wave group velocities caused by said liquid in said pipe;

generating a short duration pulse having a narrow bandwidth in a range between two adjacent frequencies of said branching frequencies;

applying said short duration narrow bandwidth pulse to a magnetostrictive sensor transmitter, thereby generating a longitudinal wave signal in said liquid filled pipe;

receiving a detected signal with a magnetostrictive sensor receiver from said liquid filled pipe; and filtering said detected signal through a narrow bandpass filter centered on said narrow bandwidth frequencies of said generated short duration pulse.

11. The method of claim 10 wherein said step of calculating dispersion curves comprises identifying a pipe geometry factor and a liquid factor, and utilizing said factors to establish dispersion characteristics for a nominal broadband signal within said liquid filled pipe.

12. The method of claim 10 wherein said step of calculating dispersion curves comprises interrogating said liquid filled pipe with a nominal broadband signal and analyzing a received signal to establish dispersion characteristics.

* * * * *